(12) United States Patent
Frej et al.

(10) Patent No.: US 9,134,282 B2
(45) Date of Patent: Sep. 15, 2015

(54) AUTOMATED INSTALLATION PROCEDURE FOR A DISPOSABLE FLOW PATH

(71) Applicant: GE HEALTHCARE BIO-SCIENCES CORP., Piscataway, NJ (US)

(72) Inventors: Kine Frej, Uppsala (SE); Niklas Edblad, Uppsala (SE); Klaus Gebauer, Uppsala (SE); Lars Kanon, Uppsala (SE)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 0 days.

(21) Appl. No.: 14/143,775

(22) Filed: Dec. 30, 2013

(65) Prior Publication Data
US 2014/0109374 A1   Apr. 24, 2014

Related U.S. Application Data

(63) Continuation of application No. 13/000,645, filed as application No. PCT/SE2009/050664 on Jun. 4, 2009, now Pat. No. 8,621,737.

(60) Provisional application No. 61/075,456, filed on Jun. 25, 2008.

(51) Int. Cl.
*G01N 30/60* (2006.01)
*B01D 15/18* (2006.01)
*G01N 30/88* (2006.01)

(52) U.S. Cl.
CPC .............. *G01N 30/60* (2013.01); *B01D 15/18* (2013.01); *G01N 2030/8804* (2013.01); *Y10T 29/49771* (2015.01); *Y10T 29/49826* (2015.01)

(58) Field of Classification Search
CPC ........... G01N 30/60; G01N 2030/8804; Y10T 29/49826; Y10T 29/49771; B01D 15/18
USPC ............ 29/407.05, 592.1, 825; 210/646, 656; 604/5.01
See application file for complete search history.

(56) References Cited

U.S. PATENT DOCUMENTS

| 4,468,329 A | * | 8/1984 | Shaldon et al. | ............... 210/651 |
| 4,711,715 A | * | 12/1987 | Polaschegg | ................... 210/103 |
| 4,997,570 A | * | 3/1991 | Polaschegg | ................... 210/646 |

(Continued)

FOREIGN PATENT DOCUMENTS

| JP | 09005300 A | 1/1997 |
| JP | 10318803 A | 12/1998 |

(Continued)

OTHER PUBLICATIONS

Search Report from corresponding CN Application No. 200980125056.7 dated Jan. 25, 2013.

(Continued)

*Primary Examiner* — Carl Arbes
(74) *Attorney, Agent, or Firm* — Parks Wood LLC; Collen A. Beard, Esq.

(57) ABSTRACT

This invention provides an automated installation procedure for assembling a disposable flow path: providing a disposable flow path comprising tubing and a plurality of sensors onto a re-usable instrument; qualifying said tubing and said plurality of sensors to be on the flow path based on a standard; and determining if the tubing and the plurality of sensors comply with characteristics and performance according to limits for specifications or acceptance criteria.

9 Claims, 4 Drawing Sheets

(56) References Cited

U.S. PATENT DOCUMENTS

| | | | |
|---|---|---|---|
| 5,344,568 A | * | 9/1994 | Kitaevich et al. ............. 210/645 |
| 6,029,495 A | | 2/2000 | Munetaka |
| 6,456,955 B1 | | 9/2002 | Andrews et al. |
| 6,554,789 B1 | * | 4/2003 | Brugger et al. ............. 604/6.11 |
| 6,579,253 B1 | * | 6/2003 | Burbank et al. ............. 604/5.01 |
| 6,955,655 B2 | * | 10/2005 | Burbank et al. ............. 604/5.01 |
| 2001/0037079 A1 | * | 11/2001 | Burbank et al. ............. 604/6.09 |
| 2008/0116122 A1 | | 5/2008 | Wheelwright et al. |

FOREIGN PATENT DOCUMENTS

| | | |
|---|---|---|
| JP | 2004515770 A | 5/2004 |
| WO | WO 02/47009 | 6/2002 |
| WO | WO 2007/067882 | 6/2007 |
| WO | 2008005907 A2 | 1/2008 |
| WO | WO 2008/064242 | 5/2008 |
| WO | 2009017814 A2 | 2/2009 |

OTHER PUBLICATIONS

Unofficial English translation of Office Action issued in connection with corresponding JP Application No. 2011-516217 on Sep. 3, 2013.

AKTAReady System, Datafile 28-9159-86 AA [online], GE Healthcare, 2008 [retrieved on Oct. 16, 2009]. Retrieved from http://www.apczech.cz/pdf/2009/01_AKTAREADY.pdf.

Validation support and services, Data File, Validation 18-1104-73, Amersham Bioscience, [retrieved on Oct. 14, 2009]. Retrieved from http://www/ebiotrade.com/GE/AKTAclub7/1.PDFs/18110473.pdf.

* cited by examiner

AUTOMATED INSTALLATION PROCEDURE FOR A DISPOSABLE FLOW PATH

FIELD OF THE INVENTION

The present invention relates to an automated installation procedure for a disposable flow path.

BACKGROUND OF THE INVENTION

Generally, chromatography is the collective term for a family of techniques that may be used in a laboratory in order to separate mixtures. This laboratory technique usually involves sending a mixture dissolved in a "mobile phase" through a stationary phase, where this stationary phase separates the analyte to be measured from other molecules in the mixture and allows it to be isolated.

There are several types of chromatography, such as gas or liquid chromatography. Gas chromatography is a separation technique in which the mobile phase is a gas. Gas chromatography is always carried out in a column, which is typically in a packed mode or capillary mode. Liquid chromatography is a separation technique in which the mobile phase is a liquid. The liquid chromatography can be carried out either in a column or a plane. Present day liquid chromatography generally utilizes very small packing particles and a relatively high pressure is referred to as high performance liquid chromatography ÄKTAready™ is a liquid chromatography system using disposable flow paths, i.e. ÄKTAready™ flow paths, manufactured by GE Healthcare in Uppsala, Sweden. The ÄKTAready™ system is based on proven liquid chromatography techniques, such as ion exchange, affinity chromatography, and hydrophobic interaction. This ÄKTAready~ system includes a disposable flow path system with UNICORN™ software that enables it to perform automated liquid chromatography. The system is characterized by a re-usable instrument that is equipped with a clean, preferably pre-sterilized, flow path prior to operation. By exchanging the flow path in between chromatographic runs and processes, the need for cleaning, cleaning validation and the risk for cross-contamination is eliminated. The flow path comprises all wetted parts in fluid contact during operation, including tubing, sensor components, fluid treatment components (e.g. air trap) and connectors.

However, there are problems with using the disposable flow path system in the ÄKTAready™ system, because the manual interaction of the user with the system during replacement of the disposable flow path may lead to improper installation (or removal) of components of the flow path system. For example, the availability of different tubing sizes of the flow path components may lead to malfunction of the system if wrong parts are installed by the user and there is no procedure for automatic recognition of the flow path components in place that may prevent the user from using a wrongly installed system. Also, if the components are not installed properly then the analyte may not be properly measured from other molecules and it may not be isolated. Additionally, there is a problem of qualifying newly installed flow path components according to their specification limits, i.e. the sensor components, prior to the chromatographic run in a safe and failure proof manner.

Further, there is another problem with the disposable flow path in that a "traditional" Installation Qualification and Operation Qualification would "contaminate" the flow kit and it would not be "clean" enough to be used for purification without doing a cleaning in place procedure. With the ÄKTAready™ system the Installation and Operation Qualification are completed by utilizing the complementary flow kit to qualify the performance of the cabinet only.

Therefore, there is a need for a system and method that enables the user to install components of the flow path system and qualify the functionality of the system components in order for the analyte (or product) to be properly measured from other molecules in the mixture and to allows the analyte (or product) to be isolated as intended.

SUMMARY OF THE INVENTION

The present invention has been accomplished in view of the above-mentioned technical background, and it is an objective of the present invention to provide an automated installation procedure for a disposable flow path of a chromatography column.

In a preferred embodiment of the invention, an automated installation procedure for assembling a flow path is disclosed. The procedure includes: providing a disposable flow path including tubing and a plurality of sensors onto a re-usable instrument; qualifying said tubing and said plurality of sensors to be on the disposable flow path based on a standard; and determining if the tubing and the plurality of sensors comply with characteristics and performance according to limits for specifications or acceptance criteria.

In another preferred embodiment of the invention, a computer implemented method for assembling a disposable flow path is disclosed. The method includes: providing a disposable flow path comprising tubing and a plurality of sensors onto a re-usable instrument; qualifying said tubing and said plurality of sensors to be on the disposable flow path based on a standard; and determining if the tubing and the plurality of sensors comply with characteristics and performance according to limits for specifications or acceptance criteria.

BRIEF DESCRIPTION OF THE DRAWINGS

These and other advantages of the present invention will become more apparent as the following description is read in conjunction with the accompanying drawings, wherein.

DETAILED DESCRIPTION OF THE INVENTION

The presently preferred embodiments of the invention are described with reference to the drawings, where like components are identified with the same numerals. The descriptions of the preferred embodiments are exemplary and are not intended to limit the scope of the invention.

Figure 1:
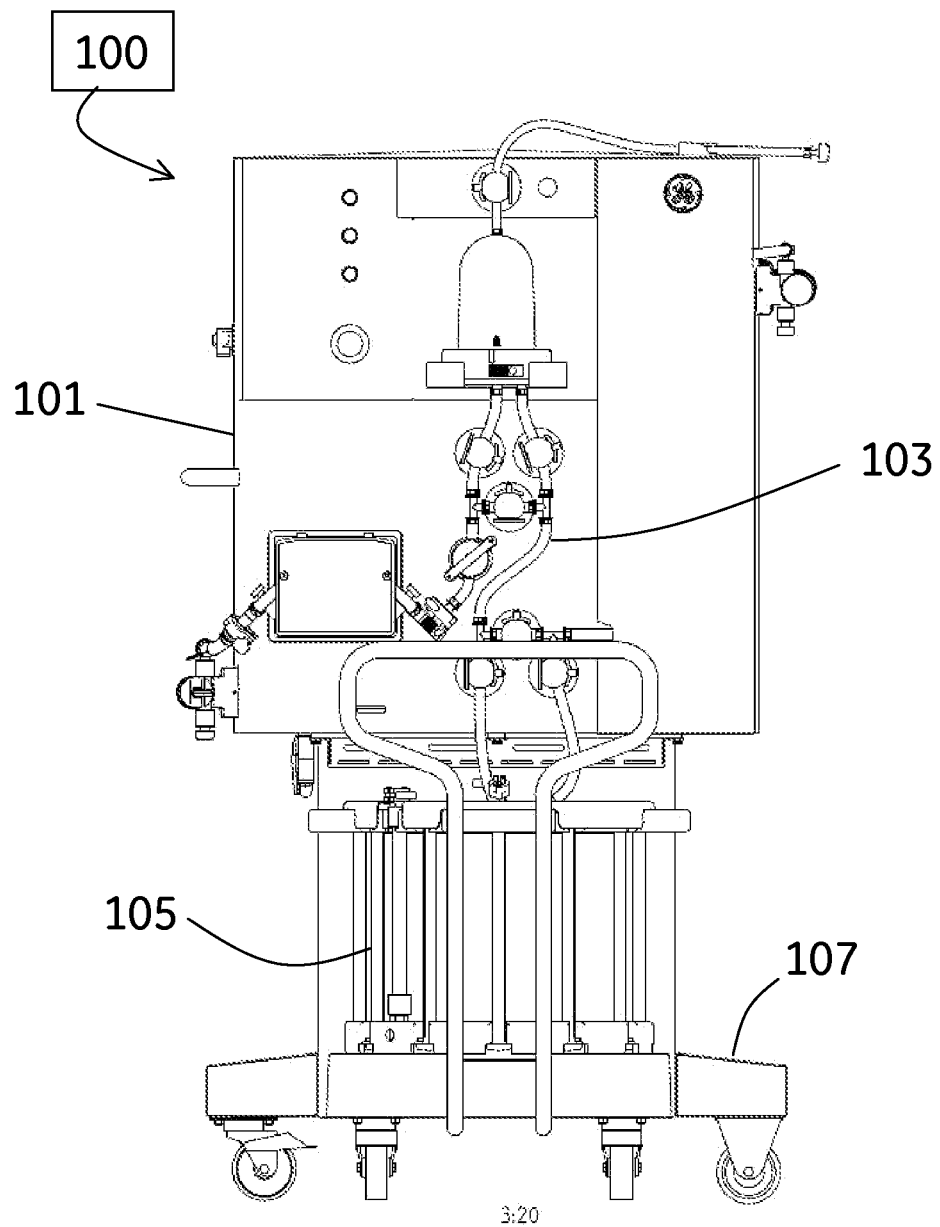
FIG. 1 is a schematic of a typical ÄKTAready™ system in accordance with an embodiment of the invention.

FIG. 1 illustrates a schematic of the typical ÄKTAready™ system. The ÄKTAready™ system is an isocratic, low pressure, automated liquid chromatography system that utilizes disposable ÄKTAready™ flow paths. The ÄKTAready™ system is based on proven liquid chromatography techniques, such as ion exchange, affinity chromatography and hydrophobic interaction. The ÄKTAready™ system is biocompatible and hygienic, and meets all and cGMP (current Good manufacturing practice) demands for Phase I-III in drug development and final-scale production. This ÄKTAready™ system 100 includes: an ÄKTAready™ cabinet unit 101, an ÄKTAready™ flow path 103, a Ready to Process column 105, a column trolley 107 and UNICORN™ software (not shown).

Figure 2:
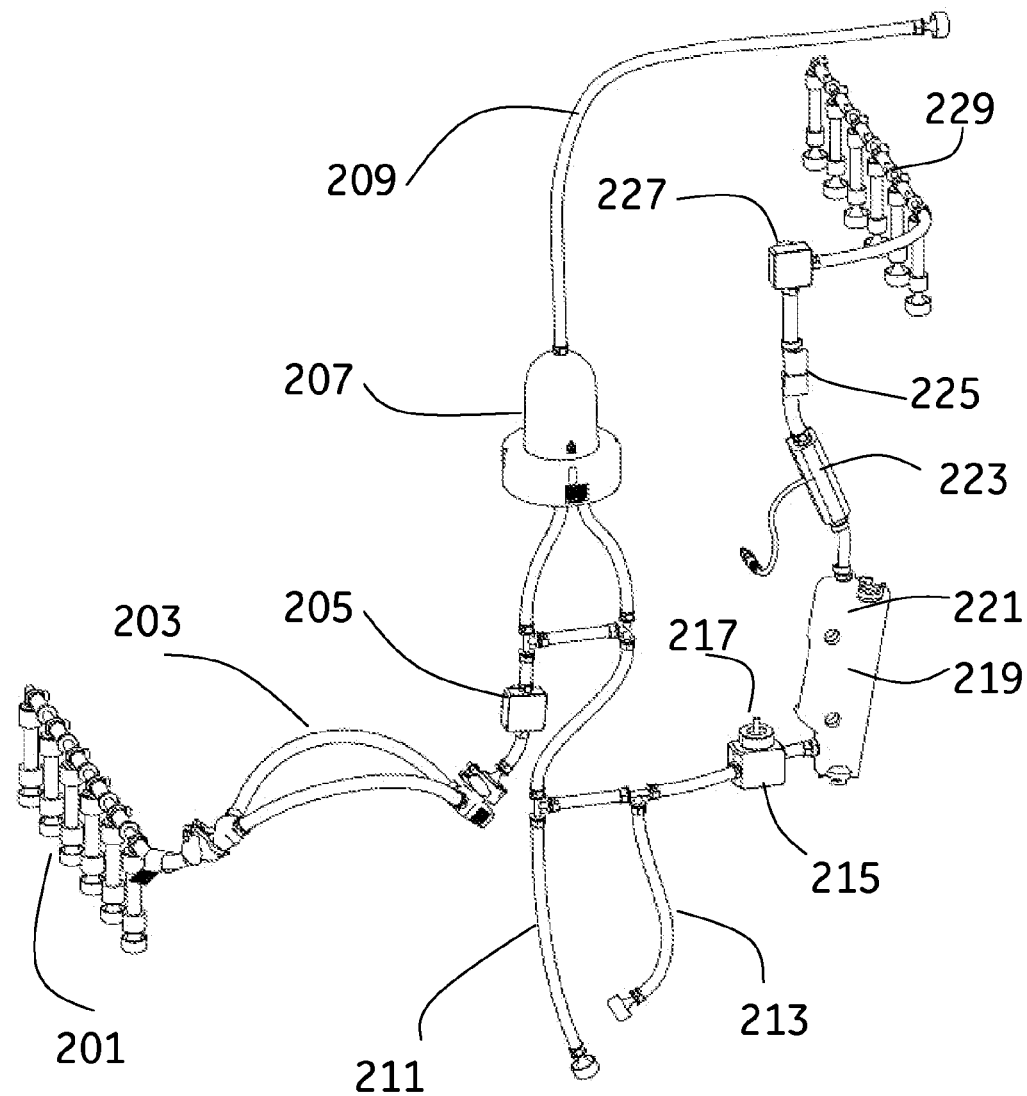
FIG. 2 is a schematic of a disposable flow path used on the re-usable ÄKTAready™ instrument of FIG. 1 in accordance with the invention.

FIG. 2 is a schematic of a flow-kit of the ÄKTAready™ system. Flow path 103 also referred to as flow path 200 includes: an inlet manifold 201, a pump tubing 203, a flow cell for pressure sensor 205, an air trap 207, an air vent tubing 209, a column inlet connection 211, a column outlet connection 213, a flow cell for pressure sensor 215, a pH electrode 217, a flow meter cell 219, a temperature cell 221, a conductivity sensor 223, an ultraviolet flow cell 225, a flow cell for pressure sensor 227 and an outlet manifold 229. Inlet manifold 201 has 6 inlets corresponding to sanitary connectors (TC), which are connected to the pump tubing 203. Pump tubing 203 is a double pump tubing used for mounting a peristaltic pump. Also, pump tubing 203 increases efficiency and reduces pulsation.

Pump tubing 203 is coupled to the flow cell for pressure sensor 205. The flow cell for pressure sensor 205 measures the pressure generated by the pump and pump tubing 203, respectively. Also, the flow cell for pressure sensor 205 is connected to the air trap 207, which allows for removal of air in buffers and sample. The air trap 207 is filled (air is evacuated) by pressing an AIR VENT button. The air vent tubing 209 is connected to the air trap 207, where the air vent tubing 209 is used for ventilation of air to/from the air trap 207. The column inlet connection 211 is also connected to the air trap 207, where the connector to column inlet tubing is a sanitary TC connector. The column outlet connection 213 is connected to the column inlet connection 211, where the column outlet connection 213 acts as the connector to column outlet tubing. All external connections of the flow path at inlets and outlets may equally be equipped with aseptic connectors that provide aseptic connections in a non-aseptic environment, thereby maintaining flow path sterility.

Next to the column outlet connection 213 is the flow cell for pressure sensor 215; this flow cell for pressure sensor 215 measures the pressure between the pump and the column. A pH electrode 217 can be mounted on the flow cell for pressure sensor 215. This pH electrode 217 measures the pH of the liquid. The flow meter cell 219 is connected to the flow cell for pressure sensor 215, where the flow meter cell 219 measures liquid velocity by using ultrasound. The temperature cell 221 is connected to the flow meter cell 219, where the temperature cell contains a surface prepared for measuring temperature by means of emitted infrared light detection. Next to the temperature cell 221 is the conductivity sensor 223 that measures the conductivity of the liquid. The ultraviolet (UV) flow cell 225 is located next to the conductivity sensor 223, where the UV flow cell is used as a UV detector. The flow cell for pressure sensor 229 is connected to the UV flow cell 225, where the flow cell for pressure sensor 229 is a flow cell for safety pressure sensor that measures pressure in the liquid after the sensors. The outlet manifold 227 is connected to the flow cell for pressure sensor 229, where the outlet manifold has 6 outlets corresponding to TC connectors.

Figure 3:
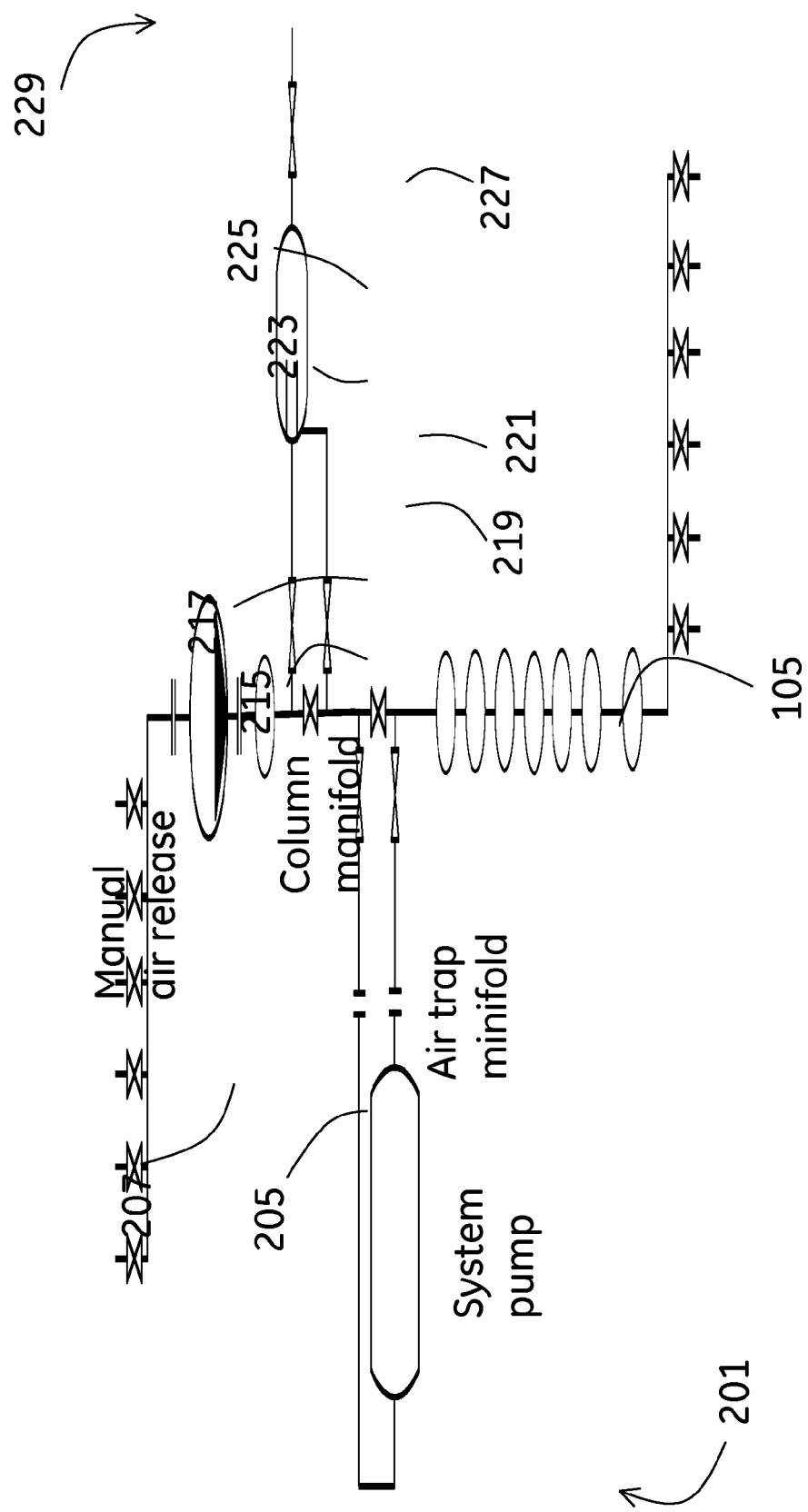
FIG. 3 is a schematic of the flow scheme the ÄKTAready™ system of FIG. 2 in accordance with invention.

FIG. 3 shows a schematic of the ÄKTAready™ flow path as liquid flows through a typical ÄKTAready™ system. Inlet valves of the inlet manifold 201 (FIG. 2) opens the appropriate inlet for the sample or buffer. The sample or buffer may be referred to as a liquid. The system pump connected to the pump tubing 203 delivers the liquid to the column 105 (FIG. 1) via the pressure sensor 205, and, if preferred, via the air trap 207 where air in the liquid is removed. There are two sets of valves for the inlet manifold 201 and the outlet manifold 229 and two additional sets of valves between the pump tubing 203 and the column 105: the air trap 207 manifold, which allows for bypassing the air trap 207, and the column manifold, also allows for bypassing the column 105.

Downstream the column 105, the liquid passes through a second pressure cell 215 (FIG. 2), which has an integrated flow cell for the pH electrode 217. The liquid then continues through the flow meter cell 219 with integrated temperature measurement 221, the conductivity cell 223, and the UV flow cell 225. The last sensor in the path is a third pressure flow cell for pressure sensor 227. Downstream the flow cell for pressure sensor 227, the liquid continues via the tubing of the outlet manifold 229, where valves divert the liquid to either waste or fraction collection. At the outlet manifold 229, the ÄKTAready™ system works under a pressure of max 0.95 bar. Between pump tubing 203 and column 105 the pressure is max 5 bar, and between column 105 and outlet manifold 229 the pressure is max 3 bar. The different pressure zones are monitored by flow cell for pressure sensors 205, 215 and 227.

Figure 4:
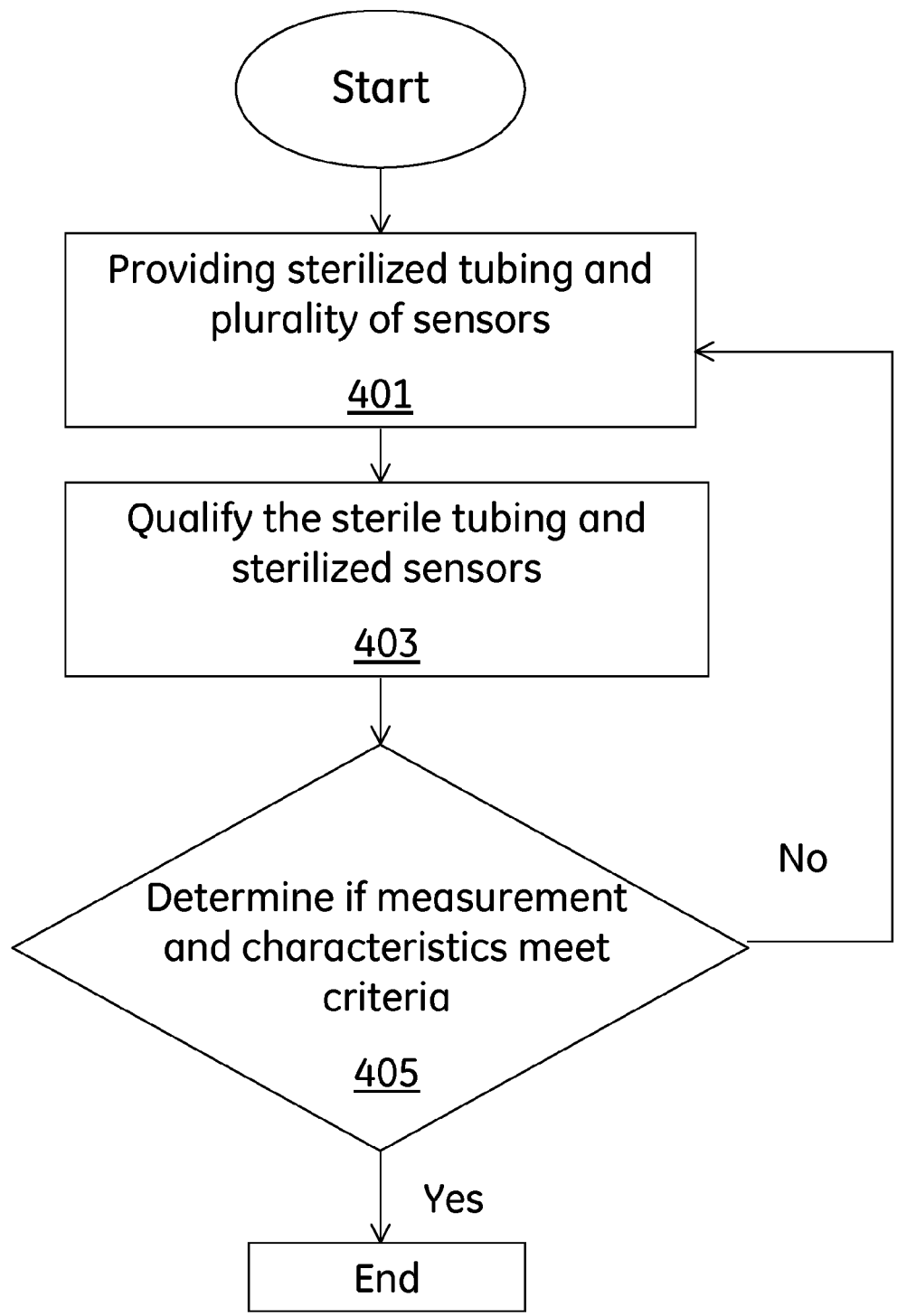
FIG. 4 is a flow-chart that depicts an automated installation procedure for assembling a disposable flow path in accordance with the invention.

FIG. 4 is a flow-chart of a computer automated installation procedure of a disposable flow path of the ÄKTAready™ system of FIG. 1 in accordance with invention. The UNICORN™ software, which is the standard software stored on the processor, memory or database of the ÄKTAready™ system that controls the ÄKTAready™ system, is the software that will control the operation of the disposable flow path procedure. Disposable means that the flow path will only be used for a single use or single batch, where there will be no cleaning or re-utilization of the flow path after it is used once. Specifically, the wizard was created to guarantee that flow paths and Ready to Process columns are correctly installed every time and to be applicable in a Good Manufacture Procedure (GMP) environment. In order to guarantee that a flow path or a column is correctly installed, the method wizard dialog is built up with detailed installation steps that are followed by a user.

At block 401, the computer provides a step by step guidance for a proper installation of all flow path components, for example a pump tubing 203 (FIG. 2), flow cell for pressure sensor 205, flow cell for pressure sensor 215 and flow cell for pressure sensor 227 on the flow path 103. Flow path 103 or flow-kit may also be referred to as a non-disposable instrument or a re-usable instrument on the ÄKTA™ system 100. The pump tubing 203, flow cell for pressure sensor 205, flow cell for pressure sensor 215 and the flow cell for pressure sensor 227 are sterilized by gamma irradiation utilizing the standard means of gamma sterilizing components. Next, at block 403 there is a qualification test of the tubing and aforementioned sensor to be on the flow path based on the standard.

The test is performed in a predefined order and at some steps if the test fail the test procedure immediately ends and the user is instructed to go through the troubleshooting guide with probable causes described. First, the flow meter cell 219 is tested for proper connection to the transducers. If this test fails the test procedure is immediately ended. After this step the complete system and used inlets during test procedures are primed (filled with liquid). The next step is to determine if the correct size of the flow kit is selected (High flow or Low flow) if the system detects that different size is installed compared to selected in UNICORN™ the test ends, this is done by measuring the flow rate measured in flow meter cell 219 with a specific Flow rate percentage is set on the pump. Next step is testing the UV flow cell 225, 1 M NaCl in 1% acetone in purified water is now pumped through the flow kit, the signal from the UV flow cell 225 is measured and tested if within the predetermined acceptance interval. The method continues regardless if the test is a failed or passed. After this the conductivity cell 223 is tested with the same solution as in previous step in a similar way but with different interval since now the measured conductivity of the liquid is tested. The method continues regardless if the test is a failed or passed. After these steps the three pressure sensors are tested, starting with pressure sensor 205 followed by pressure sensor 215 and pressure sensor 227. Different back pressures are generated by running the pump in different speeds. Each pressure sensor is tested individually and can result in a pass or fail, the procedure will continue regardless of outcome of these steps. All passed and failed tests will be summarized together with raw data in a report that can be printed out automatically.

In another example, this qualification checks that the correct size of tubing is installed, that flow rate and system capacity specifications are met with the flow path and that the flow meter provides expected functionality. Further, sensor functionality is verified by pumping sequentially a number of test solutions through the system that are characterized by different properties in regard to conductivity, light absorbance etc.

Next, at block 405 there is a determination if a plurality of components associated with the tubing and the aforementioned sensors provide measurement characteristics and performance in accordance with limits for specifications or acceptance criteria. This is done by automatic evaluation of the test data obtained in block 403 by the UNICORN™ control system of the ÄKTAready™ system. In detail, experimental data recorded in the different steps of the qualification test (block 403) is compared with acceptance limits to qualify the respective flow path component. A report is generated that documents all qualification data and serves the GMP documentation needs of the user.

If the tubing and sensor components do provide measurement characteristics and performance in accordance with limits for specifications or acceptance criteria, then the process ends, where the report is generated and the system is ready for use. In the case where the tubing and sensors do not provide measurement characteristics and performance in accordance with limits for specifications or acceptance criteria then the process would return to block 401 and a different flow path may need to be installed. At this point, a report is automatically generated by the ÄKTAready™ device that will provide a pass or failure of the functionality for the tested disposable flow path.

While the qualification and the potential failure of sensor components in block 405 primarily depends on the production quality assurance and specifications of the sensor components itself, it is the automatic guidance of manual interaction by the user during flow path installation provided by block 401 that is crucial for preventing potential errors and risks that are associated with the use of a disposable flow path compared to using a non-disposable flow path and system.

This invention provides an automated installation procedure for assembling a disposable flow path. The user is able to provide a tubing and plurality of sensors to a flow path. Then the user is able to qualify the tubing and plurality of sensors and to automatically determine if tubing or components associated with the tubing and if the plurality of sensors comply with characteristics and performance according to limits for specifications or acceptance criteria. Thus, the user is provided with a simple worry free method to install sterilized tubing and a sterilized plurality of sensors onto a flow path that is quality tested.

Although the present invention has been described above in terms of specific embodiments, many modification and variations of this invention can be made as will be obvious to those skilled in the art, without departing from its spirit and scope as set forth in the following claims. In particular, the described invention may also be applied to the removal of a used flow path from the system prior to disposal. Further, disposable tubing and components are preferably pre-sterilized when used in biopharmaceutical applications.

What is claimed is:

1. An automated installation procedure for assembling a disposable flow path comprising:
   providing tubing and a plurality of sensors to be installed onto a re-usable instrument;
   qualifying the tubing and the plurality of sensors in the disposable flow path based on a standard;
   determining if the tubing and the plurality of sensors comply with characteristics and performance according to limits for specifications or acceptance criteria by comparing experimental data recorded in the qualifying step with acceptance limits to qualify the respective flow path component; and
   generating a report that documents qualification data.

2. The method of claim 1, wherein the disposable flow path is pre-sterilized.

3. The method of claim 1, wherein the flow path includes an inlet manifold, a pump tubing and a main part.

4. The method of claim 1, further comprising generating a report if the tubing and the plurality of sensors has passed or failed a functionality test.

5. The method of claim 1, wherein the sterilized plurality of sensors include components for measurement of at least one of the types for measuring pressure, conductivity, UV absorbance and flow rate.

6. The method of claim 1, wherein the tubing and plurality of sensors are sterilized.

7. The method of claim 6, wherein the sterilized tubing and the sterilized plurality of sensors are gamma-sterilized.

8. The method of claim 1, wherein the tubing is a pump tubing of a peristaltic pump.

9. A computer-implemented image processing method for assembling a disposable flow path comprising:
   providing tubing and a plurality of sensors to be installed onto a re-usable instrument;
   qualifying the tubing and the plurality of sensors in the flow path based on a standard;
   determining if the tubing and the plurality of sensors comply with characteristics and performance according to limits for specifications or acceptance criteria by comparing experimental data recorded in the qualifying step with acceptance limits to qualify the respective flow path component; and
   generating a report that documents qualification data.

* * * * *